United States Patent
Boularot et al.

(10) Patent No.: US 10,722,167 B2
(45) Date of Patent: Jul. 28, 2020

(54) METHOD, AN OPTICAL PROBE AND A CONFOCAL MICROSCOPY SYSTEM FOR INSPECTING A SOLID ORGAN

(75) Inventors: Nicolas Boularot, Champigny-sur-Marne (FR); Magalie Genet, Franois (FR); France Schwarz, Paris (FR)

(73) Assignee: Mauna Kea Technologies, Paris (FR)

( * ) Notice: Subject to any disclaimer, the term of this patent is extended or adjusted under 35 U.S.C. 154(b) by 0 days.

(21) Appl. No.: 13/496,526

(22) PCT Filed: Sep. 17, 2010

(86) PCT No.: PCT/IB2010/002653
§ 371 (c)(1),
(2), (4) Date: Apr. 4, 2012

(87) PCT Pub. No.: WO2011/033390
PCT Pub. Date: Mar. 24, 2011

(65) Prior Publication Data
US 2012/0184842 A1  Jul. 19, 2012

Related U.S. Application Data

(60) Provisional application No. 61/243,425, filed on Sep. 17, 2009.

(51) Int. Cl.
*A61B 5/00* (2006.01)
(52) U.S. Cl.
CPC ............ *A61B 5/415* (2013.01); *A61B 5/0068* (2013.01); *A61B 5/0071* (2013.01);
(Continued)
(58) Field of Classification Search
CPC ..... A61B 5/0071; A61B 5/0068; A61B 5/415; A61B 5/6848; A61B 1/043; A61B 5/416; A61B 5/418; A61B 5/0084
(Continued)

(56) References Cited

U.S. PATENT DOCUMENTS 4,985,029 A * 1/1991 Hoshino ................ A61B 18/22
606/16
5,231,684 A * 7/1993 Narciso, Jr. ............. G02B 6/32
385/33
(Continued)

FOREIGN PATENT DOCUMENTS

EP   0735391 B1 * 10/1996
EP   1707134 A2    10/2006
(Continued)

OTHER PUBLICATIONS

International Search Report from PCT/IB2010/002653 dated Mar. 1, 2011 (5 pages).
(Continued)

*Primary Examiner* — Angela M Hoffa
*Assistant Examiner* — Helene Bor
(74) *Attorney, Agent, or Firm* — Osha Liang LLP

(57) ABSTRACT

A method to inspect a solid organ in a subject includes introducing a needle in a predetermined area of the solid organ, inserting an optical probe through a lumen of the needle, and imaging the predetermined area using the optical probe. An optical probe to inspect a solid organ in a subject, the optical probe being intended to be positioned in the solid organ through a needle, the optical probe includes an optical fiber bundle, a ferule to protect the distal tip of the optical fiber bundle, the ferule comprising a shank and a head, and a sheath wrapping the fiber bundle and the shank, wherein the head of the ferule has a length adapted for the optical probe to image the solid organ while keeping the sheath inside the needle.

21 Claims, 8 Drawing Sheets

(52) U.S. Cl.
    CPC ............ *A61B 5/0084* (2013.01); *A61B 5/418* (2013.01); *A61B 5/6848* (2013.01); *A61B 5/416* (2013.01)

(58) Field of Classification Search
    USPC ...................... 606/2; 600/478, 431; 385/139
    See application file for complete search history.

(56) References Cited

U.S. PATENT DOCUMENTS

| | | | |
|---|---|---|---|
| 5,510,895 A | 4/1996 | Sahagen | |
| 5,762,637 A * | 6/1998 | Berg | A61M 25/001 604/264 |
| 5,771,327 A * | 6/1998 | Bar-Or et al. | 385/139 |
| 6,102,905 A * | 8/2000 | Baxter | A61L 2/10 606/15 |
| 6,391,020 B1 * | 5/2002 | Kurtz et al. | 606/2 |
| 6,445,939 B1 * | 9/2002 | Swanson et al. | 600/342 |
| 6,564,087 B1 * | 5/2003 | Pitris et al. | 600/478 |
| 6,974,557 B1 * | 12/2005 | Webler | A61B 5/0084 264/261 |
| 2004/0247268 A1 | 12/2004 | Ishihara et al. | |
| 2005/0004453 A1 * | 1/2005 | Tearney et al. | 600/427 |
| 2006/0184162 A1 * | 8/2006 | Smith | 606/4 |
| 2007/0179485 A1 * | 8/2007 | Yeik | A61B 18/24 606/15 |
| 2008/0215041 A1 | 9/2008 | Zemmouri et al. | |
| 2009/0262361 A1 * | 10/2009 | Tanioka et al. | 356/479 |
| 2010/0114190 A1 * | 5/2010 | Bendett et al. | 607/3 |
| 2012/0109173 A1 * | 5/2012 | Todd | 606/170 |

FOREIGN PATENT DOCUMENTS

| | | |
|---|---|---|
| EP | 1 949 877 A1 | 7/2008 |
| JP | 2000-126115 A | 5/2000 |
| JP | 2006-271874 A | 10/2006 |
| JP | 04-500619 B2 | 7/2010 |
| WO | 90/11041 A1 | 10/1990 |
| WO | 2008/008318 A2 | 1/2008 |
| WO | 2008/137710 A1 | 11/2008 |
| WO | 2009/157289 A1 | 12/2009 |

OTHER PUBLICATIONS

Office Action dated Nov. 4, 2014, in related Japanese Application No. 2012-529357 (with translation) (6 pages).

* cited by examiner

Prior Art

Prior Art

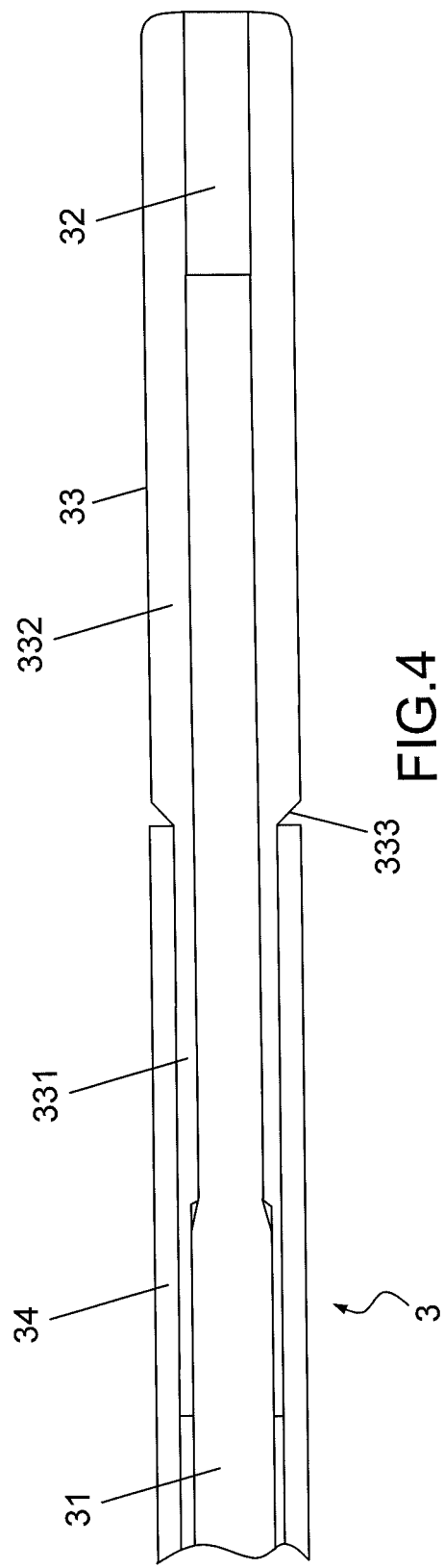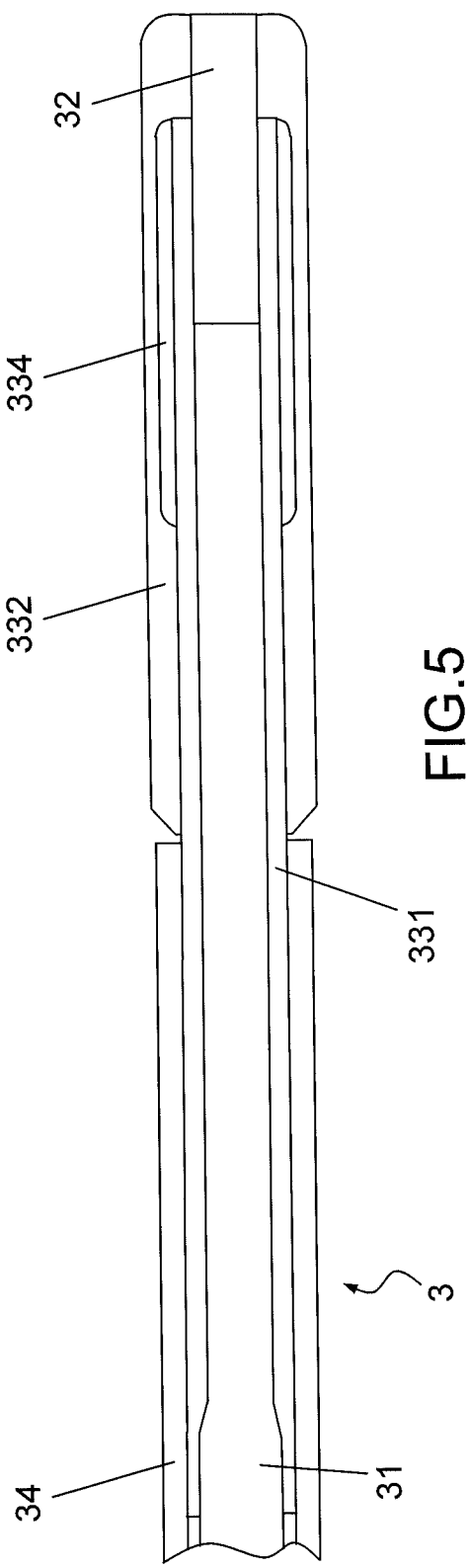

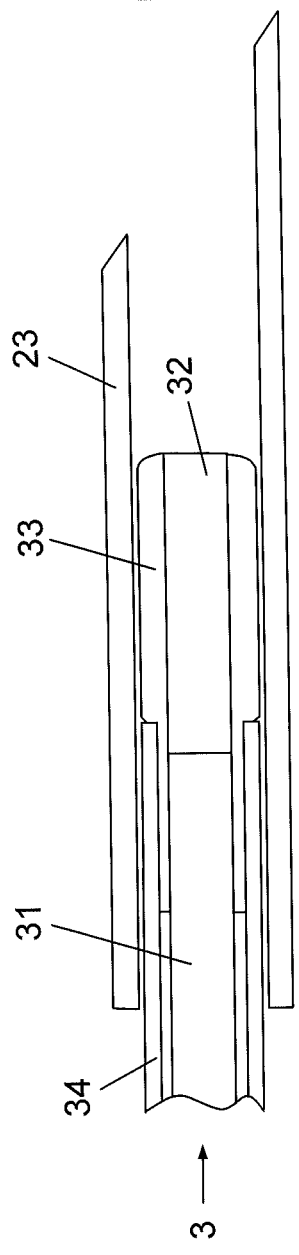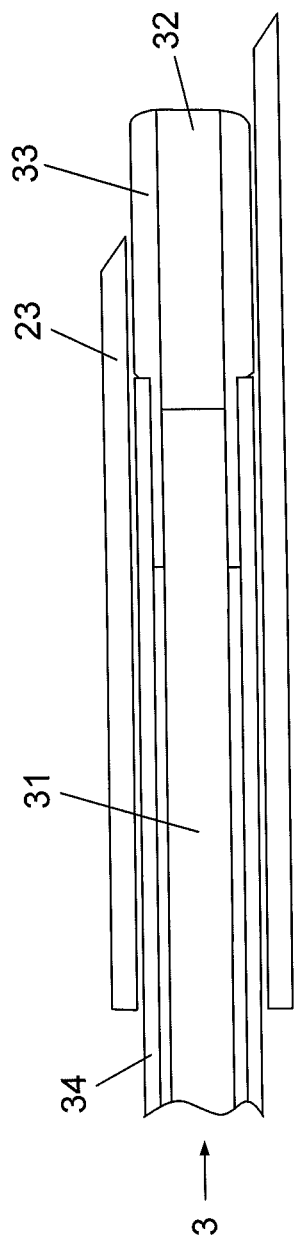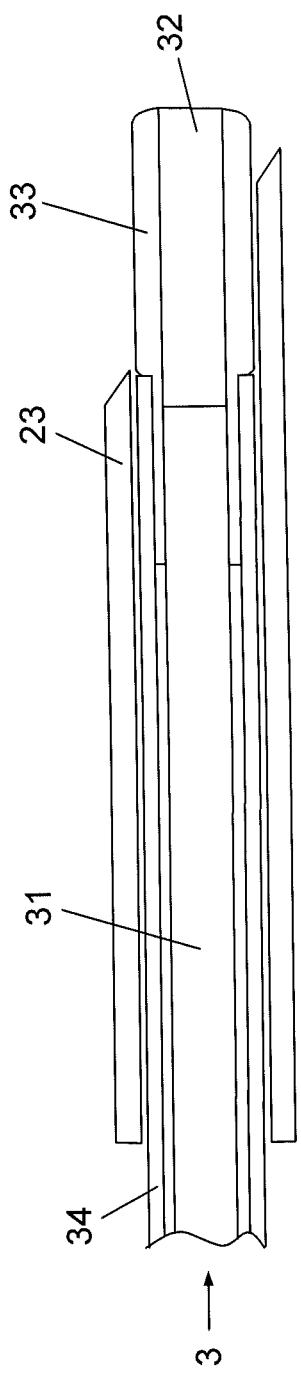

METHOD, AN OPTICAL PROBE AND A CONFOCAL MICROSCOPY SYSTEM FOR INSPECTING A SOLID ORGAN

BACKGROUND

Field of the Present Disclosure

The disclosure generally relates to organ inspection. More specifically, it relates to organ inspection of living subjects for diagnosing purpose and/or therapeutic applications.

Background Art

In the following description, a solid organ is defined as an organ that does not contain a cavity or lumen and that is not gaseous. A solid organ may for example consist of parenchyma and stroma, the latter often arranged as trabeculae or surrounding groups of parenchymatous cells to provide support (e.g. liver, kidney). A solid organ may also comprise cysts. Histological examination of suspected lesions and structural alterations in solid organs, e.g. in liver cirrhosis or staging of pancreatic malignant disease, is a continuous challenge. Radiology only offers a partial answer to this issue because Magnetic Resonance Imaging (MRI), helical Computed Tomography (CT) scan, endoscopic ultrasonography and Positron Emission Tomography (PET) only allow a low accuracy diagnosis with significant over and under-staging status. To confirm definite diagnosis, standard histopathology through biopsies remains the current standard practice.

In order to get a tissue sample on living subjects, endoscopy procedures are generally preferred. As shown on FIG. 1A, for imaging the gastrointestinal tract (GI tract), an endoscope 1 may be inserted in a subject 7 through upper or lower endoscopy. A specific endoscopy procedure, called Endoscopic UltraSound-guided Fine Needle Aspiration (EUS-FNA) is designed to provide ultrasound images of accessory full organs of the GI tract, such as the liver, the pancreas and sentinel lymph nodes. Referring now to FIG. 1B, which illustrates an EUS-FNA procedure, the endoscope 1 may access a stomach 71 at the level of a junction with a duodenum 72 through upper endoscopy. A distal tip of the endoscope 1 may comprise an ultrasound module 11 for targeting a mass 74 of a pancreas 73 with an endoscopic needle 23 inserted into a working channel of the endoscope 1.

In the present description and subsequent claims, the term "needle" is used to indicate a hollow conduit that has a tip intended to puncture organs. Preferably, the tip is beveled. In the present description and subsequent claims, the expression "endoscopic needle" is used to indicate a hollow conduit adapted to be inserted in the working channel of an endoscope. In selected embodiments, the endoscopic needle has a beveled tip.

The range of the ultrasound is marked on FIG. 1B with dashed lines. The pancreas 73 may then be punctured and penetrated by the endoscopic needle 23 in order to obtain a biopsy for diagnosis purposes. EUS-FNA procedures are common in the field of endoscopy and are used for diagnostic of lesions as well as therapeutic actions. EUS-FNA main applications include:

Pancreatic solid or cystic lesions. Solid masses or cysts can grow in the pancreas and they need to be punctured to diagnose whether they are malignant tumors or benign lesions. Liquid cysts, due to pancreatitis for instance, may also be punctured via EUS-FNA in order to be drained.

Staging of cancers, by assessing the content of the surrounding lymph nodes. Indeed in many cancers, including lung cancer, pancreatic cancer, gastric cancer or rectum cancer, metastases are often found in the lymph nodes. Therefore, puncturing the lymph nodes allows diagnosing if cancer has spread.

Other less common applications of EUS-FNA include lesions in the liver or submucosal lesions in the GI tract. EUS-FNA procedures work by using an echoendoscope (standard endoscope with an ultrasound module at its tip) to localize a suspected lesion via ultrasound images of the area surrounding the GI or respiratory tract (in the case of lesion in the respiratory tract, the procedure is called EUS-TBNA for Endoscopic UltraSound-guided TransBronchial Needle Aspiration). Then a fine endoscopic needle is inserted in the endoscope's working channel and punctures the surrounding wall (either GI tract wall, or bronchial tree) in order to reach the targeted lesion. This puncture is monitored thanks to real-time ultrasound images in order to guide the needle to the lesion while avoiding any dangerous vessel puncture. The endoscopic needles used for the puncture have varying diameters, but the most used are referred to in the art as 19G and 22G needles, whose inner diameter is about 890 µm and 560 µm respectively.

However, cytology has also major limitations including: incremental cost, risk, time needed to perform a diagnosis, lack of in vivo information such as blood flow, and limited ability to predict disease course. Fine needle aspirations are particularly limited by sampling errors due to the limited number of aspirations and delayed diagnosis because of time consuming sampling processing.

The Applicant proposes hereunder a method, an optical probe and a confocal microscopy system for inspecting solid organs capable of overcoming the aforementioned limitations and in particular to accelerate the time needed for diagnosis and/or therapy.

SUMMARY OF THE CLAIMED SUBJECT MATTER

In at least one aspect, embodiments disclosed herein relate to a method for inspecting a solid organ in a subject. The method may include the steps of introducing a needle in a predetermined area of the solid organ, inserting an optical probe through a lumen of the needle, and imaging the predetermined area by means of the optical probe.

Preferably, the step of introducing a needle in a predetermined area of the solid organ is performed before the step of inserting an optical probe through a lumen of the needle. According to an alternative embodiment, the step of introducing a needle in a predetermined area of the solid organ is performed after the step of inserting an optical probe through a lumen of the needle.

Preferably, the step of introducing the needle in the solid organ comprises puncturing the solid organ, preferably with a tip of the needle, which is preferably beveled.

According to a preferred embodiment, the step of introducing the needle in the solid organ comprises puncturing the solid organ using a stylet which is preferably preliminary inserted in the lumen of the needle, the stylet being preferably driven to protrude out of the needle and being preferably removed from the lumen before the step of inserting the optical probe through the lumen of the needle.

Preferably, the needle is percutaneously inserted in the organ.

Preferably, the solid organ is one selected from the group comprising, preferably consisting of a pancreas, a liver, a spleen, a lymph node, a prostate, a kidney, breast and ovaries.

According to a preferred embodiment, the needle is passed through a working channel of an endoscope which is preferably inserted in the subject through a natural orifice to approach the solid organ.

Preferably, the endoscope is passed through an internal incision of internal tissues to access the solid organ.

Preferably, the needle is guided using an ultrasound module. Preferably, the ultrasound module is arranged at a tip of the endoscope.

Preferably, the needle is passed through an incision of internal tissues to access the solid organ.

Preferably, the needle is guided using any of an ultrasound module, a scanner, a computed tomography scan system, a magnetic resonance imagery system or a fluoroscopy imagery system.

In at least one aspect, embodiments disclosed herein relate to an optical probe for inspecting a solid organ in a subject, the optical probe being intended to be positioned in the solid organ through a needle. The optical probe preferably comprises an optical fiber bundle; a ferule for protecting the distal tip of the optical fiber bundle, the ferule preferably comprising a shank and a head; a sheath preferably wrapping the fiber bundle and the shank. The head of the ferule has a length adapted for the optical probe to image the solid organ while keeping the sheath inside the needle.

Preferably, the optical probe further comprises an objective connected coaxially at a distal tip of the optical fiber bundle, and the ferule preferably connects the objective to the distal tip of the optical fiber bundle.

Preferably, the shank and the head of the ferule are coaxially mounted together.

Preferably, both the shank and the head of the ferule have a tubular shape defining a lumen. Preferably, the optical fiber bundle and the objective are enclosed in said lumen.

Preferably, the optical probe further comprises an external junction between the shank and the head, the external junction being chamfered.

Preferably, the shank, the head and the external junction are integrally made, preferably integrally molded with one another.

The optical probe according preferably further comprises glue preferably provided on the external junction between the head and the shank of the ferule.

Preferably, the head of the ferule extends to the tip of the objective to be in contact with the organ to image.

Preferably, the head of the ferule extends to the tip of the optical fiber bundle to be in contact with the organ to image.

Preferably, the optical fiber bundle, the ferule and the sheath each have an external diameter of preferably less than 0.9 mm, preferably less than 0.8 mm, preferably less than 0.7 mm.

Preferably, the length of the ferule is less than 8 mm, preferably less than 7 mm, preferably less than 6 mm. Preferably, the axial length of the ferule is less than 8 mm, preferably less than 7 mm, preferably less than 6 mm.

Preferably, the external diameter of the head of the ferule is substantially equal to the external diameter of the sheath.

Preferably, the optical probe further comprises a locking mechanism preventing the head of protruding out of the needle. Preferably, the locking mechanism is intended to prevent the head of protruding out of the needle more than of a predetermined length.

Preferably, an internal surface of the sheath is adapted to stick on the shank.

Preferably, the optical probe further comprises at least one hollow section, preferably a hollow volume to be filled for example with air or other suitable gas for enhancing ultrasound visualization of the optical probe.

In at least one aspect, embodiments disclosed herein relate to a confocal microscopy system for inspecting a solid organ in a subject preferably comprising a confocal microscope, and an optical probe as described above.

Other aspects and advantages of the present disclosure will be apparent from the following description and the appended claims.

BRIEF DESCRIPTION OF DRAWINGS

FIG. 4 illustrates a distal tip of an optical probe according to an embodiment of the present disclosure.

FIG. 5 illustrate a distal tip of an optical probe according to an embodiment of the present disclosure.

FIGS. 6A, 6B and 6C illustrate three positions of an optical probe according to embodiments of the present disclosure inserted in a needle according to the prior art.

DETAILED DESCRIPTION

Figure 1A:
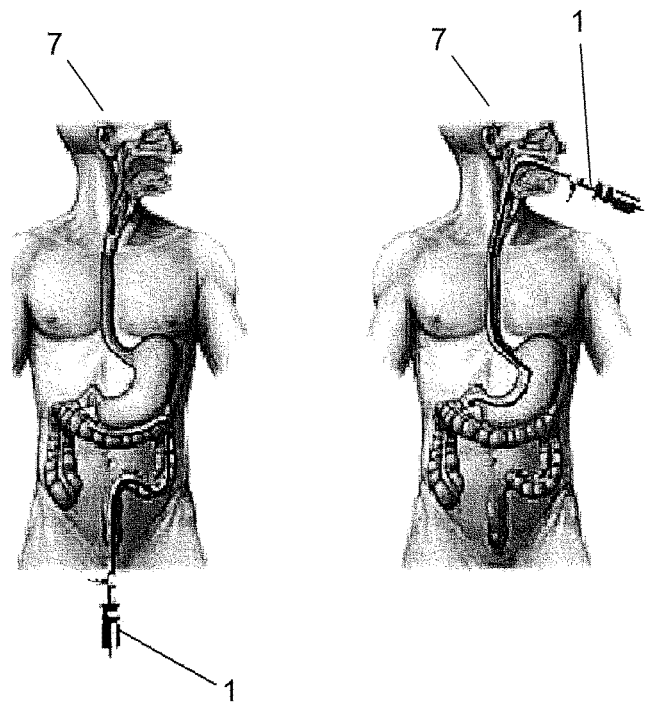
FIG. 1A illustrates a lower endoscopy and an upper endoscopy on a human body according to the prior art.
Figure 1B:
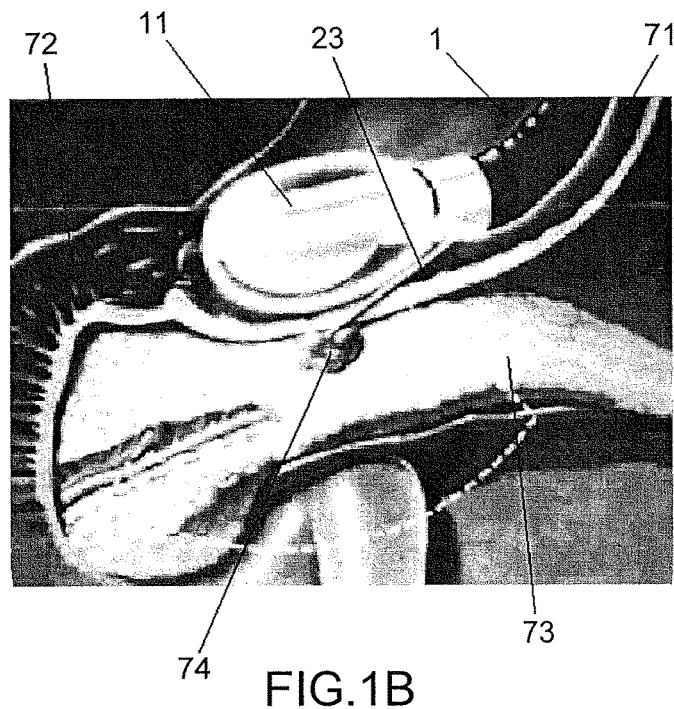
FIG. 1B illustrates a standard Endoscopic UltraSound-guided Fine Needle Aspiration technique (EUS-FNA) according to the prior art.

Specific embodiments of the present disclosure will now be described in detail with reference to the accompanying Figures. Like elements in the various Figures may be denoted by like numerals.

In a method for inspecting solid organs according to the present disclosure, a needle may be introduced in a solid organ of a subject. An optical probe inserted in a lumen of the needle may be brought in contact of a predetermined area of the organ to image the predetermined area. The optical probe may be used together with a confocal microscopy system. Imaging the organ according to this method may enable to obtain microscopic pictures of the predetermined area and may help establishing a diagnosis in real time. The solid organ may be one selected from the group consisting of a pancreas, a liver, a spleen, a lymph node, breast, ovaries, a kidney or a prostate.

The step of introducing the needle in the solid organ may comprise puncturing the solid organ, preferably with a tip of the needle. In order to facilitate the puncturing, the tip of the needle intended to puncture the organ is preferably beveled. The needle may be percutaneously inserted in the organ to image. Alternatively, the needle may be an endoscopic needle and may be passed through a working channel of an endoscope inserted in the subject for example through upper or lower GI endoscopy procedures, bronchoscopy and other endoscopic procedures (for example transrectal ultrasound, cystoscopy, etc.) in order to approach the solid organ to image. The endoscope may further be passed through an internal incision for the needle to directly access the solid organ. The needle may puncture a surrounding wall before accessing the organ to image. The step of inserting the optical probe in the needle may be performed before or after the step of puncturing the organ with the needle. The optical probe may be positioned to protrude out of the needle and may be locked on a given position using a locking mechanism.

After the puncture of the surrounding organs (for instance the stomach or duodenum in the case of a pancreatic lesion), dirt resulting from surrounding organ residuals may remain in the lumen of the needle. A stylet may be used to push the dirt out of the lumen. Advantageously, when the step of inserting the optical probe follows the puncture, the stylet may be loaded in the lumen of the needle during the organ puncture. The dirt may also be pushed out of the needle by the optical probe. Advantageously, when the step of inserting the optical probe in the needle precedes the puncture, the optical probe performs pushing out of the dirt.

In another embodiment, the solid organ may be punctured by a stylet preloaded in the lumen of the needle. The stylet may have a beveled edge to ease the organ puncture. The stylet may be driven out of the lumen of the needle to puncture a predetermined area of the solid organ. The needle may thereafter be introduced in the solid organ at the predetermined area. The stylet may be removed for the optical probe to be inserted in said lumen.

The needle may be guided to the predetermined area using ultrasound, scanner, MRI or the like in order to avoid dangerous vessel puncture. An ultrasound module may be arranged at a tip of an endoscope in order to visualize the needle when it is used through the working channel of the endoscope. The device used to perform the puncture (i.e. the needle or the stylet) may puncture the organ under direct visualization or ultrasound guidance by advancing carefully into the organ. Advantageously, when the optical probe is used together with a fluorescence fiber microscope, fluorescein may be injected intravenously for intensifying contrast enhancement. The optical probe may then be manipulated in order for a distal tip of the optical probe to touch the inner tissue of the organ.

Figure 2:
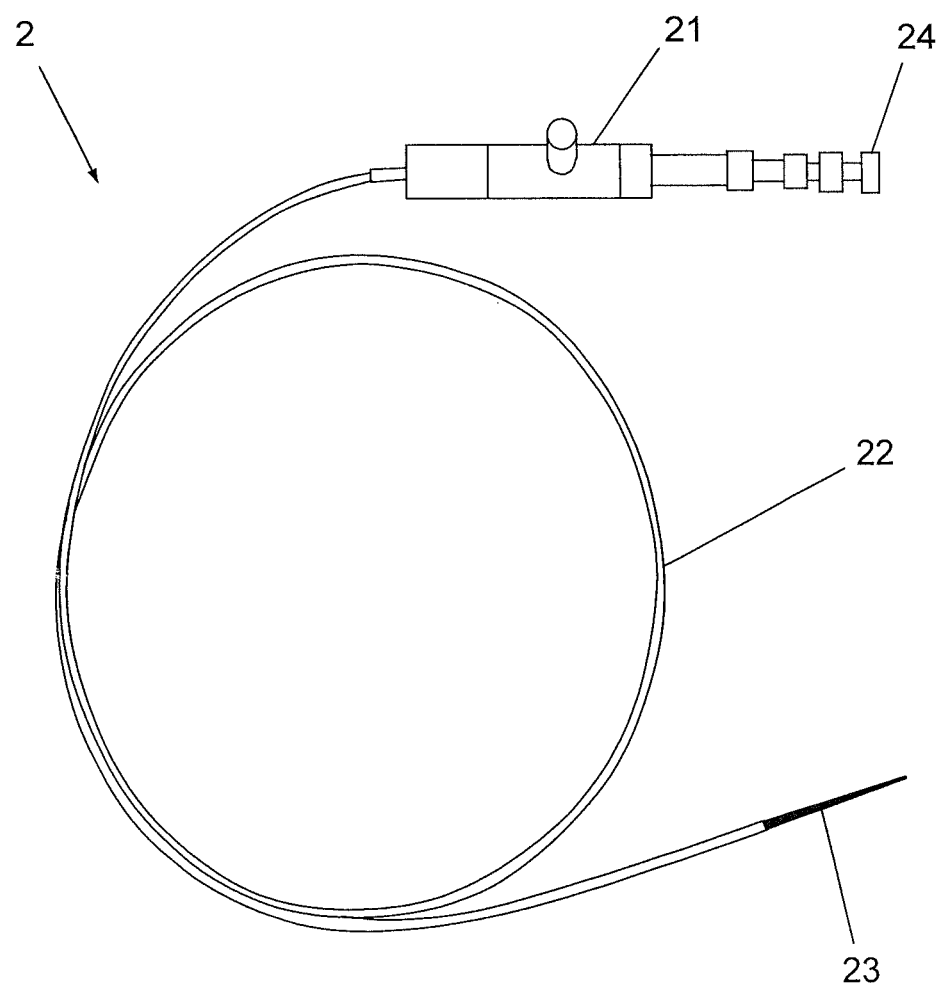
FIG. 2 shows an endoscopic needle system according to the prior art.

FIG. 2 shows an endoscopic needle system 2 that may be used for fine needle aspiration. The endoscopic needle system 2 may comprise a handle 21, a protective needle sheath 22, and an endoscopic needle 23. A stylet 24 may be inserted through an opening in a lumen of the needle. The opening may be located at an end of the handle 21. A syringe connection that may also be placed on the opening may enable to connect a syringe for aspiration of a tissue when the endoscopic needle system is used for performing tissue aspiration through EUS-FNA procedure. In order to connect the syringe, the stylet may first be removed. According to an embodiment of the present disclosure, an optical probe may be inserted through the opening in the lumen of the needle. The needle 23 may be enclosed in the sheath 22 and the handle 21 may also comprise a control system to enable controlled protrusion of the needle 23 out of the needle sheath 22. When an optical probe is inserted in the lumen of the needle 23, the position of the optical probe in the lumen may be manually adjusted by an operator. The distal tip of the needle may be beveled in order to facilitate the puncture of a predetermined organ. Preferred features of the needle may be for example: inner diameter (ID) from about 0.30 mm to 1 mm; outer diameter (OD) from about 0.6 mm to about 1.2 mm. Particularly preferred needles are the 22G needle (ID=0.56 mm; OD=0.71 mm) and the 19G needle (ID=0.89 mm; OD=1.07 mm). Those having ordinary skill will appreciate that alternative needle gauges and sizes may be used as well.

Figure 3:
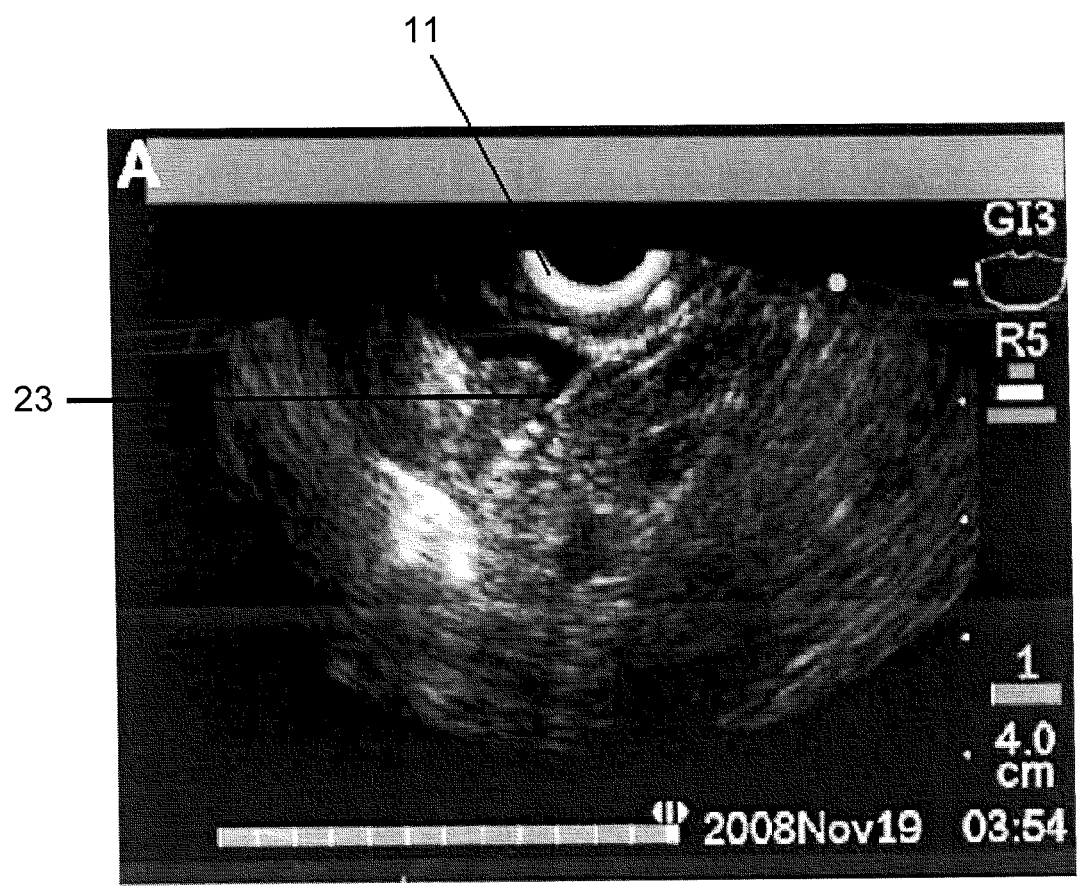
FIG. 3 illustrates an ultrasound view obtained via EUS-FNA in a pancreas according to an embodiment of the present disclosure.

The sheath 22 together with the needle 23 may be inserted into an endoscope to approach an organ. The step of puncturing the organ may be performed under ultrasound guidance. FIG. 3 illustrates an ultrasound picture of a pancreas taken via an endoscope arranged with a linear ultrasound module 11 at its tip during a puncture of a pancreas by an endoscopic needle 23.

Figure 7:
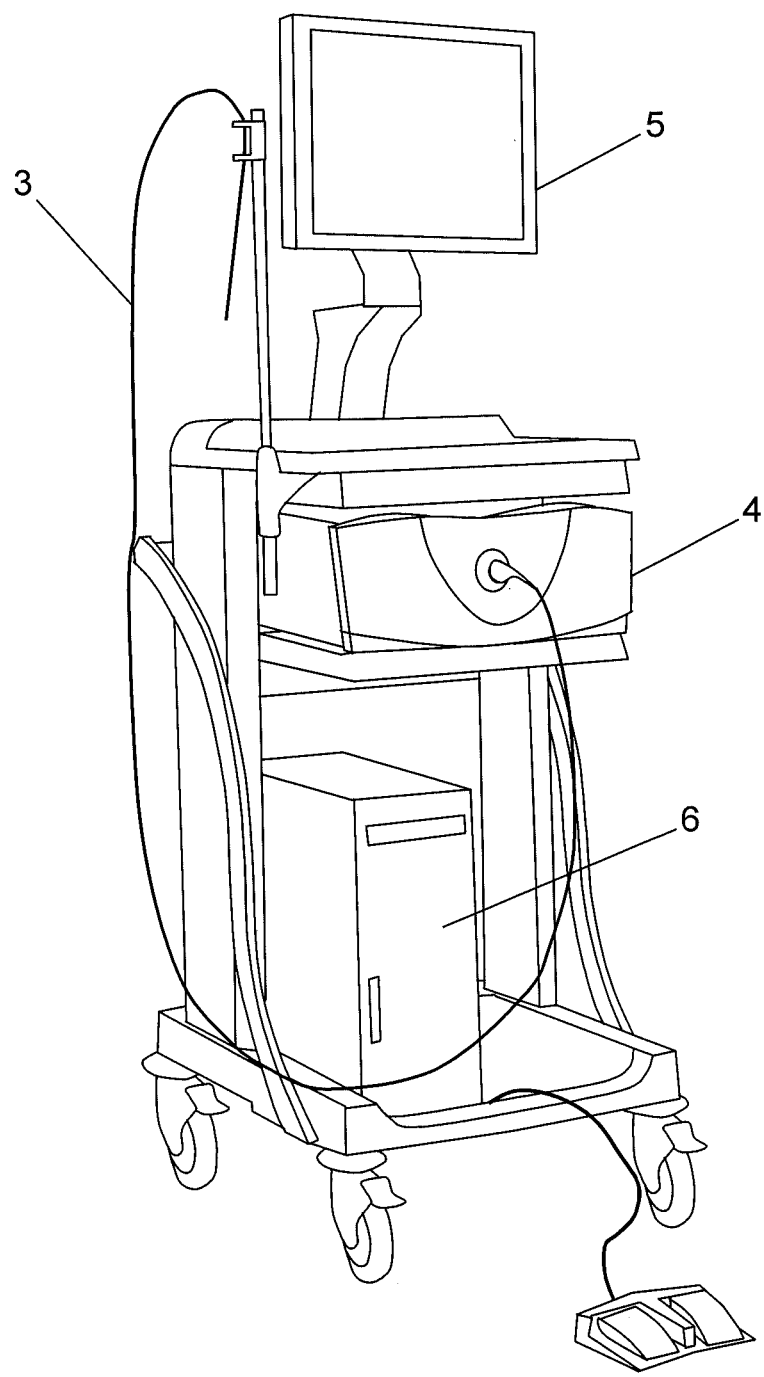
FIG. 7 illustrates a confocal microscopy system according to an embodiment of the present disclosure.

Referring to FIG. 7, an optical probe 3 according to an embodiment of the present disclosure may comprise an optical fiber bundle made of several thousands of optical fibers protected by a sheath. The fibers may, for example, have a core diameter of 2 μm and a mean core spacing of 3.3 μm. A proximal end of the optical probe may be connected for example to a real-time scanning confocal microscope 4 (such as Cellvizio® from Mauna Kea Technologies). A proximal end may also be connected to any type of fiber microscopes. Observations at cellular or micro-vascular levels with high sensitivity may also be made possible. The proximal confocal microscope 4 may include an illumination source, which may be a LASER source, capable of exciting endogenous or exogenous fluorophores. The proximal confocal microscope 4 may also include a detection channel, which permits collecting and measuring a fluorescence signal. In an embodiment, the confocal microscope is a reflection microscope collecting and measuring backscattered light. The distal objective of the optical probe 3 conjugates the distal end of the fiber bundle with a specific image plane, at a specific working distance when the optical probe is in contact with a biological tissue. When illuminated one after another by the proximal scanner, each fiber of the bundle becomes an illumination source of a small volume within the tissue. This illumination may excite endogenous or exogenous fluorescence. In addition to functioning as a source of light, the illumination fiber also collects the fluorescence signal and transmits it to the proximal scanner. There, the return beam is spatially filtered and directed to the detection channel. As a result, the optical probe and its proximal scanner perform a confocal exploration of the tissue. The resulting images may be stored and processed on a processing and storage device 6 and may also be displayed on a display device 5.

Referring now to FIG. 4, an optical probe 3 may comprise an optical fiber bundle 31, a miniaturized objective 32 coaxially mounted at a distal tip of the optical fiber bundle 31 and a ferule 33 for connecting the objective 32 to the distal tip of the optical fiber bundle 31. The ferule 33 may comprise a shank 331 and a head 332. A sheath 34 may wrap a portion of the fiber bundle 31 and the shank 331. The head 332 may extend to the tip of the objective 32 to be in contact of the organ to image and may be polished in order to limit its invasiveness. The shank 331 and the head 332 of the ferule 33 may both have a tubular shape and be coaxially arranged. The shank 331 and the head 332 may be integrally formed. The fiber bundle 31 and the objective 32 may fit in a lumen formed by arranging the shank 331 and the head 332 coaxially. The shank 331 and the head 332 may have same internal diameter. An external junction 333 between the shank 331 and the head 332 may be chamfered. Advantageously, the chamfered external junction may be covered with glue to prevent from dirt accumulation at the junction 333.

In an embodiment, the optical probe 3 may not comprise an objective and the distal tip of the fiber bundle 31 may be brought directly into contact of an organ to image. In this embodiment, the head 332 may protect the fiber bundle 31 and may extend to the distal tip of the fiber bundle 31.

As shown in FIG. 5, the optical probe 3 may comprise at least one hollow volume 334 filled with air in order to enhance ultrasound visualization of the optical probe 3. Advantageously, the air in the hollow volume may be replaced by any fluid or solid enhancing ultrasound visualization of the optical probe. The head and the shank may have a tubular shape. The external diameter of the shank 331 may substantially be equal to the internal diameter of the head 332. An internal surface of the head 332 may comprise a cavity so that the hollow volume 334 may result from assembling the shank into a lumen of the head 332.

Referring to FIG. 6A, the optical probe 3 may be inserted in a lumen of the needle 23. The optical probe 3 may be moved toward the tip of the needle 23 (FIG. 6B) in order to protrude out of the tip of the needle (FIG. 6C) for imaging a predetermined area of an organ (not shown on FIGS. 6A-C). The needle 23 may be beveled to ease the puncture of the organ. The head 332 of the optical probe may have a longitudinal length adapted for the sheath 34 to stay enclosed in the needle 23 when the tip of the head 332 is moved beyond the tip of the needle 23 in order to be put in contact with the organ. In other words, the head 332 may have an axial length such that the sheath 34 stays before the end section of the needle (preferably before the beginning of the bevel) when the tip of the head 332 projects out of the end section of the needle (after the end of the bevel, i.e. the free end of the needle 23). The head 332 may be pushed beyond the end of the bevel of about 0 to 5 mm. The bevel of the needle 23 may form an angle of about 20° to 90° relatively to a longitudinal axis of the needle 23. Preferably, the bevel of the needle 23 may be of about 20°. The head 332 may have a length of about 1 to 8 mm. The length of the head 332 of the optical probe 3 may be defined as the axial length of the head 332. Preferably, the bevel of the needle 23 may have a length greater than 2 mm. The length of the bevel may be defined as the axial length between the beginning of the bevel and the end of the bevel, i.e. the free end of the needle 23. In other words, the length of the bevel may be equal to the projection, on the longitudinal axis of the needle 23, of the beveled edge of the needle 23. The length of the head 332 of the optical probe 3 is preferably greater than the length of the bevel of the needle 23.

Experiments with first ferules having a longitudinal length of about 4 mm and second ferules having a longitudinal length of about 8 mm have shown that the first ferules ease the extraction of the probe 3 from the needle 23 especially when the needle 23 is bent, for example upon accessing lesions through the duodenum.

A safe contact between the probe 3 and the needle 23 is provided by the presence of the ferule 33 which avoids the probe 3 to be cut by the bevel of the needle 23. When the probe 3 is inserted in the needle 23, a predetermined limit of advancement of the probe 3 beyond the end of the bevel may be determined. In an embodiment, this limit position may be reached when the probe 3 protrudes from the distal tip of the needle 23 of more than 2 mm. Having the probe 3 protruding out of the bevel from 2 mm may enable to position the tip of the probe 3 in better contact with the tissue to inspect and therefore enables to obtain a good image quality. Preferably, the length of the head 332 of the optical probe 3 is superior to the length of the bevel of the needle 23 increased by the predetermined limit of advancement of the probe 3 beyond the end of the bevel.

Preferably, the head of the optical probe 3 may have a length of about 3 mm. This may advantageously improve the resistance of the optical probe 3 by preventing the sheath 34 to rub against the bevel of the needle 23. The length of the ferule may be advantageously kept lower than 12 mm for the flexibility of the endoscope and the needle to stay satisfactory.

Figure 8A:
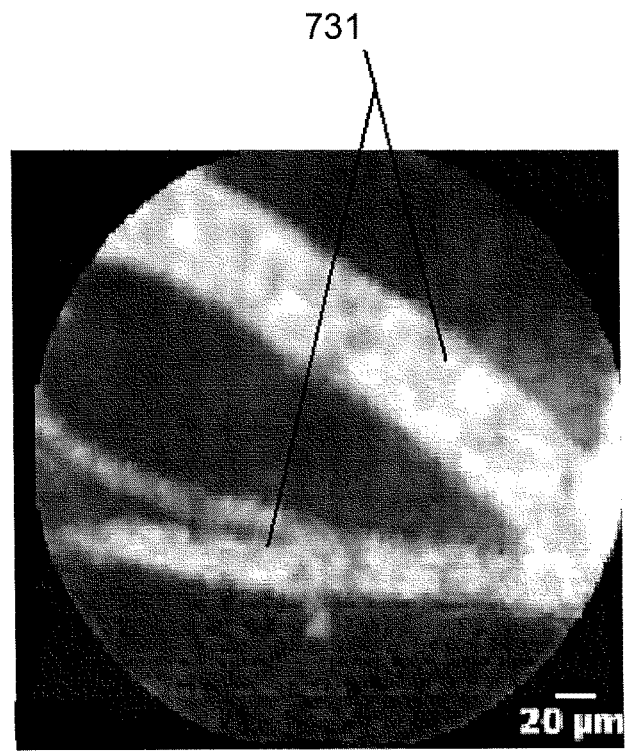
FIGS. 8A and 8B are respectively confocal images of pancreatic and hepatic blood vessels obtained using a method and the confocal microscopy system of FIG. 7 according to embodiments of the present disclosure.
Figure 8B:
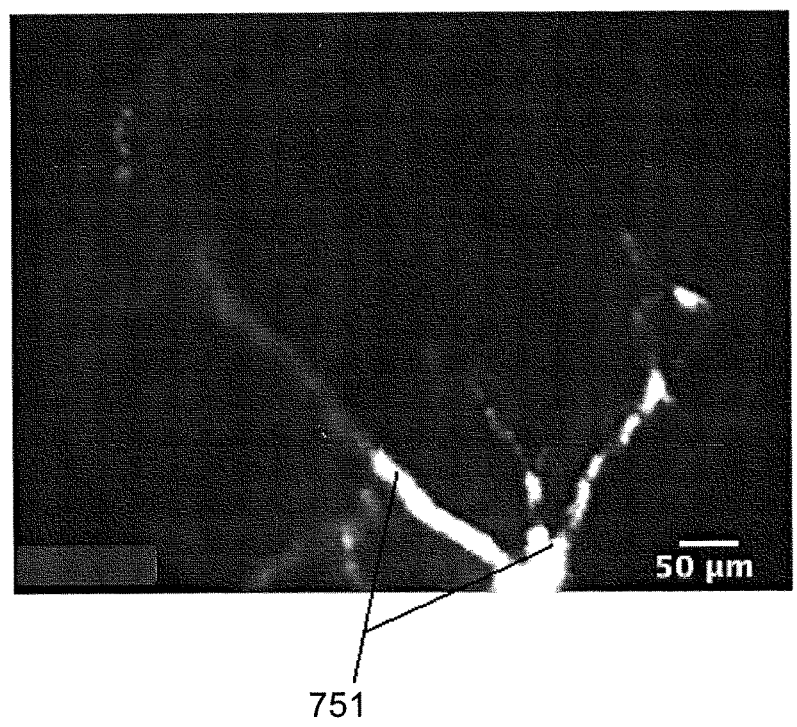

FIGS. 8A-B and FIGS. 9A-C illustrate images of solid organs obtained according to embodiments of the present disclosure. FIGS. 8A and 8B show blood vessels 731 and 751 respectively observed in a pancreas and in a liver.

Figure 9A:
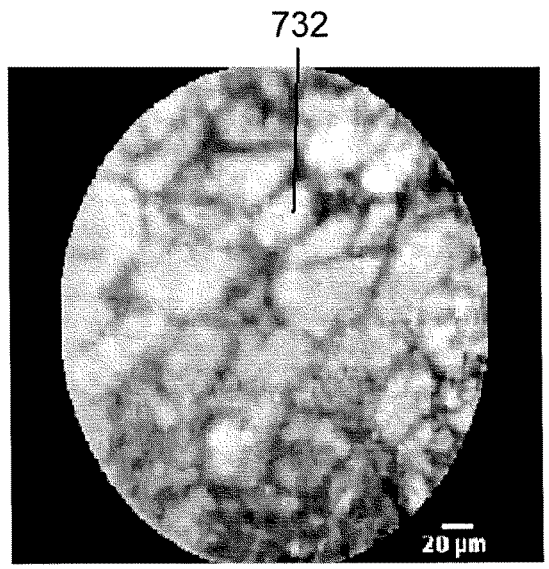
FIGS. 9A, 9B and 9C are respectively confocal images of pancreatic, hepatic and splenic cells obtained using a method and the confocal microscopy system of FIG. 7 according to embodiments of the present disclosure.
Figure 9B:
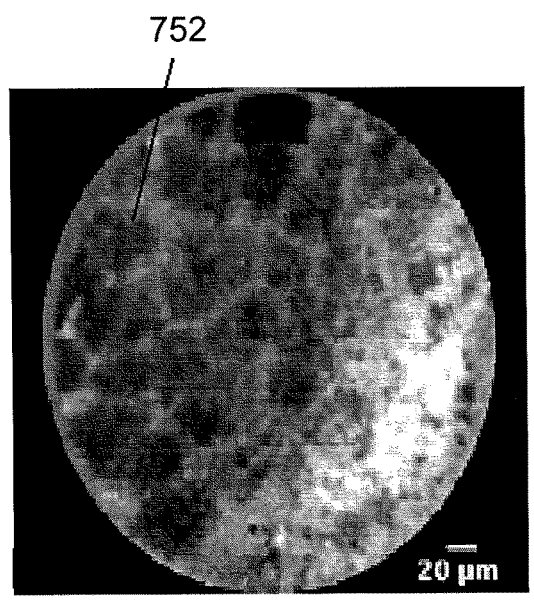
Figure 9C:
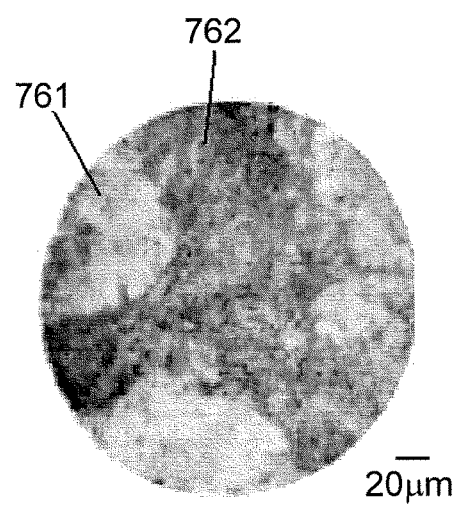

FIG. 9A has been acquired in a pancreas and shows pancreatic acini 732 which are part of the exocrine part of the pancreas. FIG. 9B has been acquired in a liver. The liver is a very vascularized organ, divided into small hexagonal structures called lobules which are themselves composed of hepatocytes 752 separated by sinusoids. FIG. 9C has been acquired in a spleen and enables to distinguish between the red pulp 762 and white pulp 761 of the spleen.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure will be limited only by the attached claims.

What is claimed is:

1. A method to image a solid organ in a subject comprising:
    introducing a needle in a predetermined area of the solid organ, wherein the solid organ is one selected from the group consisting of a pancreas, a liver, a spleen, a lymph node, a prostate, a kidney, breast and ovaries, wherein the needle comprises a beveled distal tip;
    inserting an optical probe through a lumen of the needle, such that the optical probe, after insertion, protrudes outside the lumen and beyond the beveled distal tip of the needle by at least 2 mm; and
    imaging the predetermined area using the optical probe, wherein the optical probe comprises:
    an optical fiber bundle;
    a ferule that protects a distal tip of the optical fiber bundle, the ferule comprising a shank and a head, wherein the shank and the head of the ferule have a tubular shape with a same internal diameter and are coaxially mounted;
    a sheath that wraps the fiber bundle and the shank, wherein the head of the ferule has a length adapted for the optical probe to image the solid organ while keeping the sheath inside the needle, the solid organ being at least one selected from a group consisting of a pancreas, a liver, a spleen, a lymph node, a prostate, a kidney, a breast, and an ovary,
    wherein an external diameter of the head of the ferule is equal to an external diameter of the sheath; and
    a single objective directly connected coaxially at a distal tip of the optical fiber bundle, wherein the ferule connects the single objective to the distal tip of the optical fiber bundle, and wherein the ferule completely surrounds the single objective up to a distal tip of the single objective at a distal tip of the optical probe, wherein the single objective is forward facing and captures an image in a coaxial direction of the optical probe, and the optical fiber bundle includes:

a flexible portion where the optical fiber bundle is surrounded by the sheath and not surrounded by the ferule, and a rigid portion where the optical fiber bundle is surrounded by both the sheath and the ferule, wherein the external diameter of the flexible portion is the same as the external diameter of the rigid portion.

2. The method according to claim 1, wherein introducing the needle in the solid organ comprises puncturing the solid organ with a tip of the needle.

3. The method according to claim 2, further comprising percutaneously inserting the needle in the organ.

4. The method according to claim 1, wherein introducing the needle in the solid organ comprises puncturing the solid organ using a stylet preliminary inserted in the lumen of the needle, the stylet being driven to protrude out of the needle and being removed from the lumen before inserting the optical probe through the lumen of the needle.

5. The method according to claim 1, further comprising passing the needle through a working channel of an endoscope inserted in the subject through a natural orifice to approach the solid organ.

6. The method according to claim 5, further comprising passing the endoscope through an internal incision of internal tissues to access the solid organ.

7. The method according to claim 5, further comprising guiding the needle using an ultrasound module arranged at a tip of the endoscope.

8. The method according to claim 1, further comprising passing the needle through an incision of internal tissues to access the solid organ.

9. The method according to claim 1, further comprising guiding the needle using at least one of an ultrasound module, a scanner, a computed tomography scan system, a magnetic resonance imagery system or a fluoroscopy imagery system.

10. An optical system to image a solid organ in a subject, comprising:

a needle;

an optical probe positioned through the needle, wherein the optical probe comprises:

an optical fiber bundle;

a ferule that protects a distal tip of the optical fiber bundle, the ferule comprising a shank and a head, wherein the shank and the head of the ferule have a tubular shape with a same internal diameter and are coaxially mounted;

a sheath that wraps the fiber bundle and the shank, wherein the head of the ferule has a length adapted for the optical probe to image the solid organ while keeping the sheath inside the needle, the solid organ being at least one selected from a group consisting of a pancreas, a liver, a spleen, a lymph node, a prostate, a kidney, a breast, and an ovary, wherein an external diameter of the head of the ferule is equal to an external diameter of the sheath; and a single objective directly connected coaxially at a distal tip of the optical fiber bundle, wherein the ferule connects the single objective to the distal tip of the optical fiber bundle, and wherein the ferule completely surrounds the single objective up to a distal tip of the single objective at a distal tip of the optical probe, wherein the single objective is forward facing and captures an image in a coaxial direction of the optical probe, and the optical fiber bundle includes:

a flexible portion where the optical fiber bundle is surrounded by the sheath and not surrounded by the ferule, and a rigid portion where the optical fiber bundle is surrounded by both the sheath and the ferule, wherein the external diameter of the flexible portion is the same as the external diameter of the rigid portion.

11. The optical system according to claim 10, further comprising an external junction between the shank and the head, the external junction being chamfered.

12. The optical system according to claim 11, wherein the shank, the head and the external junction are integrally molded.

13. The optical system according to claim 11 further comprising glue provided on the chamfered external junction between the head and the shank of the ferule.

14. The optical system according to claim 10, wherein the head of the ferule extends to the tip of the single objective to be in contact with the organ to image.

15. The optical system according to claim 10, wherein the head of the ferule extends to the tip of the optical fiber bundle to be in contact with the organ to image.

16. The optical system according to claim 10, wherein the optical fiber bundle, the ferule and the sheath each have an external diameter of less than 0.9 mm.

17. The optical system according to claim 10, wherein the length of the ferule is less than 8 mm.

18. The optical system according to claim 10, further comprising a locking mechanism preventing the head of protruding out of the needle more than of a predetermined length.

19. The optical system according to claim 10, wherein an internal surface of the sheath is adapted to stick on the shank.

20. The optical system according to claim 10, further comprising at least one hollow section to be filled with air for enhancing ultrasound visualization of the optical probe.

21. A confocal microscopy system for inspecting a solid organ in a subject comprising:

a confocal microscope, a needle; and an optical probe positioned through the needle, wherein the optical probe comprises:

an optical fiber bundle;

a ferule that protects a distal tip of the optical bundle, the ferule comprising a shank and a head, wherein the shank and the head of the ferule have a tubular shape with a same internal diameter and are coaxially mounted;

a sheath that wraps the fiber bundle and the shank, wherein the head of the ferule has a length adapted for the optical probe to image the solid organ while keeping the sheath inside the needle, the solid organ being at least one selected from a group consisting of a pancreas, a liver, a spleen, a lymph node, a prostate, a kidney, a breast, and an ovary, wherein an external diameter of the head of the ferule is equal to an external diameter of the sheath; and a single objective directly connected coaxially at a distal tip of the optical fiber bundle, wherein the ferule connects the single objective to the distal tip of the optical fiber bundle, and wherein the ferule completely surrounds the single objective up to a distal tip of the single objective at a distal tip of the optical probe, wherein the single objective is forward facing and captures an image in a coaxial direction of the optical probe, and the optical fiber bundle includes:

a flexible portion where the optical fiber bundle is surrounded by the sheath and not surrounded by the ferule, and a rigid portion where the optical fiber bundle is surrounded by both the sheath and the ferule, wherein the external diameter of the flexible portion is the same as the external diameter of the rigid portion.

* * * * *